(12) United States Patent
Hnat et al.

(10) Patent No.: US 7,357,037 B2
(45) Date of Patent: Apr. 15, 2008

(54) STRAIN SENSING SYSTEM

(75) Inventors: William P. Hnat, Floyds Knobs, IN (US); John F. Naber, Prospect, KY (US); Kevin M. Walsh, Louisville, KY (US)

(73) Assignee: Orthodata Technologies LLC, Prospect, KY (US)

( * ) Notice: Subject to any disclaimer, the term of this patent is extended or adjusted under 35 U.S.C. 154(b) by 66 days.

(21) Appl. No.: 11/226,023

(22) Filed: Sep. 14, 2005

(65) Prior Publication Data

US 2006/0032314 A1 Feb. 16, 2006

Related U.S. Application Data

(63) Continuation-in-part of application No. 10/616,599, filed on Jul. 10, 2003, now abandoned.

(60) Provisional application No. 60/394,607, filed on Jul. 10, 2002.

(51) Int. Cl.
*G01N 3/00* (2006.01)
(52) U.S. Cl. ....................................................... 73/795
(58) Field of Classification Search .................. 73/795
See application file for complete search history.

(56) References Cited

U.S. PATENT DOCUMENTS

| 5,585,571 | A | 12/1996 | Lonsdale et al. |
| 6,706,005 | B2 * | 3/2004 | Roy et al. ..................... 600/594 |
| 7,047,074 | B2 * | 5/2006 | Connelly et al. ............. 607/36 |
| 7,160,258 | B2 * | 1/2007 | Imran et al. ................. 600/593 |
| 7,161,484 | B2 * | 1/2007 | Tsoukalis ............... 340/539.12 |
| 2002/0082665 | A1 | 6/2002 | Haller et al. |
| 2005/0288604 | A1 * | 12/2005 | Eigler et al. ................. 600/561 |

FOREIGN PATENT DOCUMENTS

| WO | 005610 A1 | 3/2000 |
| WO | 0056210 A1 | 3/2000 |
| WO | 0137726 A1 | 5/2001 |
| WO | 2004005872 A2 | 1/2004 |

* cited by examiner

*Primary Examiner*—Max Noori
(74) *Attorney, Agent, or Firm*—Alexander P. Brackett; Middleton Reutlinger

(57) ABSTRACT

The present invention provides a system 10 for measuring and remotely monitoring strain in an element 1 having a strain sensor 20, a telemetry circuit 40 for transmitting strain data to a remote location, and a reader module 60 for transmitting energy to the telemetry circuit and receiving said data.

11 Claims, 6 Drawing Sheets

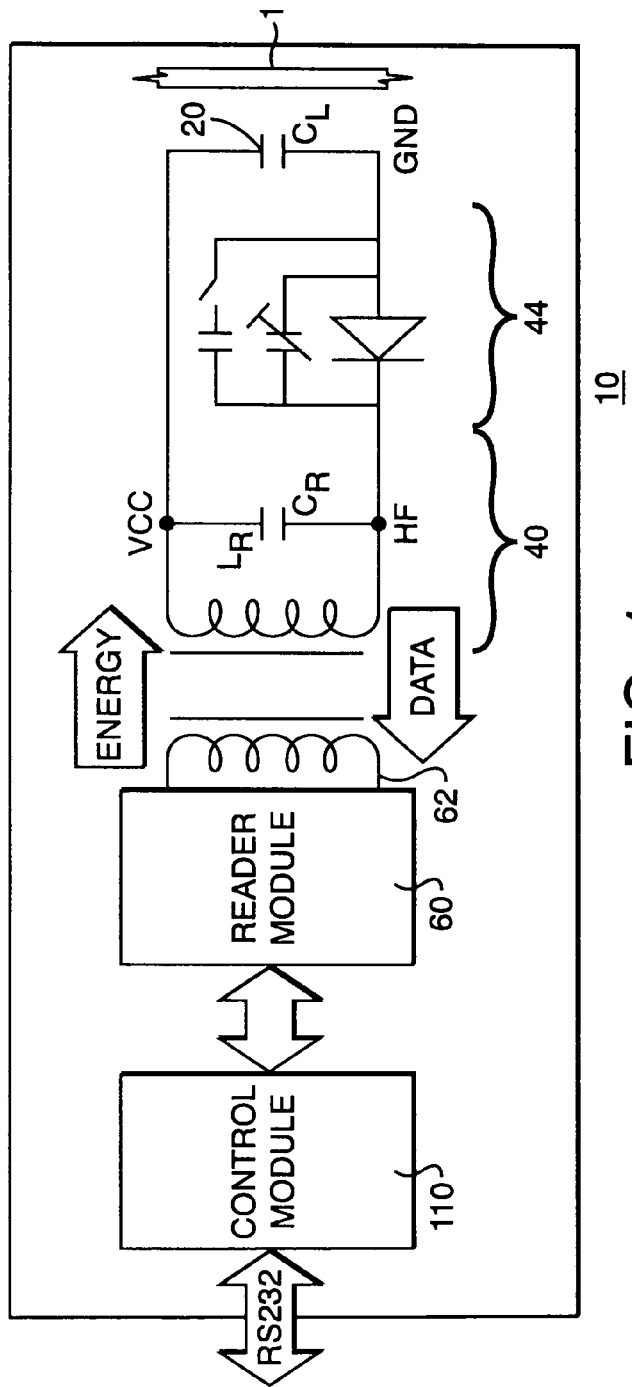
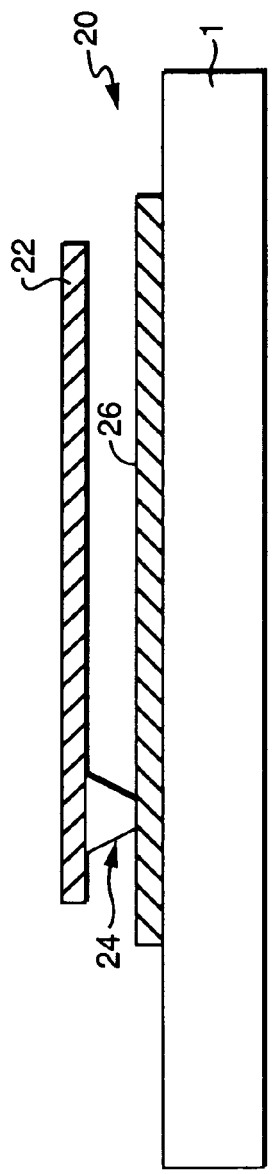
FIG. 1
FIG. 2

STRAIN SENSING SYSTEM

This application is a continuation-in-part of and claims priority to and benefit from U.S. utility patent application Ser. No. 10/616,599 of Hnat et al. entitled "Strain Sensing System", filed Jul. 10, 2003, which in turn claims priority to and benefit from U.S. provisional patent application Ser. No. 60/394,607 filed Jul. 10, 2002 and entitled "Real Time Monitoring System For Spinal Fusion".

FIELD OF THE INVENTION

The present invention relates generally to a system for sensing and remotely monitoring strain in an element. More specifically, the present invention relates to a biomedical implant that incorporates a strain sensor and a telemetry circuit, and a remote reader module of measuring and monitoring strain in, for example, an orthopedic device located within a human or animal subject such that the resultant strain data can be analyzed to determine the progress of a healing injury or monitor the long term effectiveness of an implanted device.

BACKGROUND OF THE INVENTION

Many modern surgical techniques for the repair of damaged skeletal structure utilize implanted orthopedic devices affixed to the skeletal structure to lend support and rigidity thereto until the normal healing process progresses sufficiently that the structure is capable of its intended use. For example, spinal fusion surgery often involves implantation of a bio-compatible stainless steel or titanium spinal fusion implant comprised of a plurality of rods affixed to the damaged spine proximate the damaged area, usually by pedicle screws. The implant is designed to stabilize and support the spine until fusion occurs.

Presently there are several techniques available to a physician to monitor the healing or fusion process in an orthopedic implant. Common diagnostic tools include radiography, computer tomography (CT) and magnetic resonance imaging (MRI) scans, and of course exploratory surgery. Radiography, CT scans and MRI scans all are quite limited in their ability and accuracy in monitoring fusion progress due to the difficulty encountered in interpreting the scan results, even by experienced medical practitioners. Exploratory surgery is, of course, quite reliable for viewing fusion progress but is highly undesirable because of the various risks associated with an additional surgery. While some methods of measuring the progress of fusion in a patent presently exist, no known methods have the ability to monitor strain in an orthopedic device or other element (and thus the progress of the fusion taking place) under both static and dynamic loading conditions.

By carefully monitoring and quantifying the progress of spinal fusion, patients are able to return to normal activities sooner without risk of compromising the fusion process. The result is a reduction in doctor visits, decreased medical costs, and a reduction in lost work time and the attendant cost savings resulting therefrom. The average time for spinal fusion to occur is between 6 and 12 months. A real-time monitoring system for spinal fusion will eliminate the need for more costly procedures such as CT and MRI scans and provides surgeons with valuable information during the treatment process. Elimination of a single follow-up CT scan alone could save over $000 per patient. Furthermore, fusion failures can be diagnosed more quickly and accurately thereby permitting the orthopedic surgeon to take corrective measures immediately when the fusion process is not progressing space.

SUMMARY OF THE INVENTION

The present invention provides a miniature sensor for measuring strain in a loaded element with a radio frequency telemetry circuit utilized to transmit data derived from the output of the sensor to a remotely located reader. The telemetry circuit and sensor may be powered via inductive coupling from the reader so that no power source is required to be placed in vivo in implantation applications. Furthermore, a bio-compatible housing may be used to encapsulate the sensor and telemetry components and provide a convenient method for mounting the system on orthopedic implant devices, as well as provide some measure of strain amplification.

Commercially available orthopedic devices such as spinal fixation rods can be quipped with the proposed monitoring system and used to measure the strain in the device, thereby providing the surgeon with a reliable and cost effective method to determine the success of the orthopedic implant in vivo. The monitoring system may also be used as a warning system for implant failures since the rod strains will necessarily decrease as healing progresses. Rod strain levels that do not decrease over time, increase somewhat, or change abruptly could be indicative of implant failure. The monitoring system may also be used with orthopedic screws, pins, plates, and joint implants.

The present invention provides a physician with the ability to monitor the spinal fusion process by measuring quantitatively the spinal fixation rod strains. The in vivo load transfer from the spinal fusion rod to the spine is monitored in real time using a miniature strain sensor placed either directly or indirectly on the surface of the rod. This data is then transmitted outside the body using the internal telemetry circuit and external reader, and evaluated instantaneously by the surgeon. IN a successful fusion surgery, as the spine fuses the load on the spine is transferred from the rod to the spine, thereby lowering the monitored strain on the implant rod surface. The load transfer for a normal spinal fusion should be gradual and any deviation would indicate either non-fusion or possible failure of a rod or pedicle screw used to secure the rod to the spine.

It is therefore one object of the instant invention to provide a system for measuring and monitoring strain in an element.

A further object of the invention is a system that remotely monitors strain in a loaded element.

A further object of the invention is a system for measuring in vivo strain on an orthopedic device.

A further object of the invention is a system for measuring in vivo strain in an orthopedic device.

A further object of the invention is a system for measuring in vivo strain in an orthopedic device in real time.

Other uses, advantages, and features of the instant invention will become apparent after reading the detailed description of the preferred embodiments taken in conjunction with the accompanying drawing figures.

BRIEF DESCRIPTION OF THE DRAWING FIGURES

FIG. 1 is a block diagram of the strain measuring system in accordance with the present invention.

FIG. 2 is a block diagram of a capacitance sensor in accordance with the present invention.

DETAILED DESCRIPTION OF THE PREFERRED EMBODIMENTS

Figure 3:
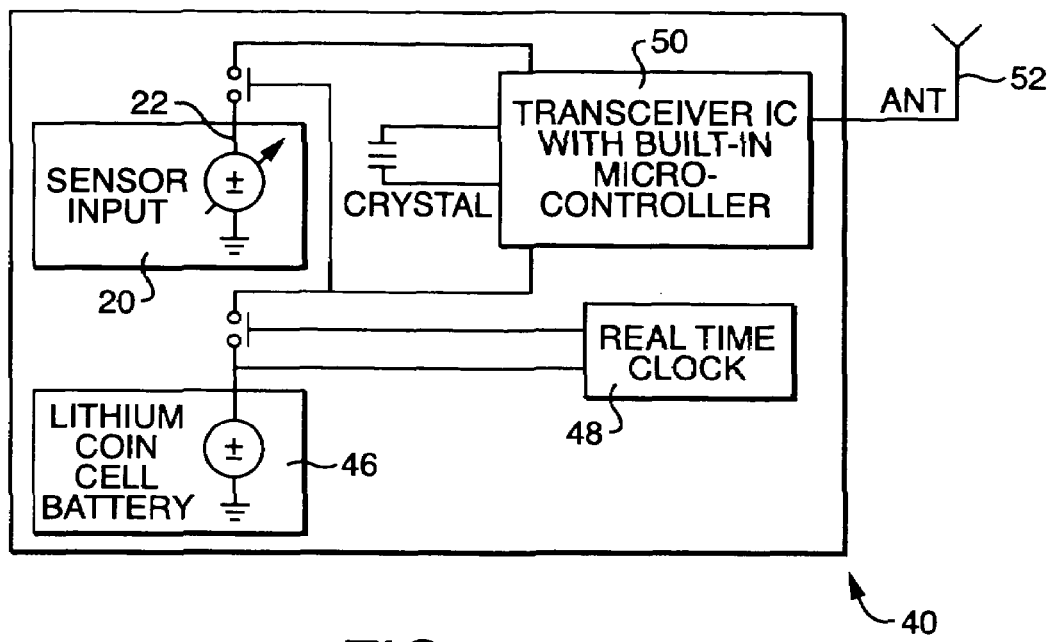
FIG. 3 is a block diagram of the strain measuring system in accordance with the present invention.

Referring to FIG. 1 and in accordance with one embodiment of the instant invention, a system 10 for measuring and remotely monitoring strain in an element 1 subject thereto includes a sensor 20 capable of measuring static and dynamic strain in the element 1, a telemetry circuit 40 that transmits sensor 20 data, and a remotely located reader module 60 for receiving the transmitted sensor data. The sensor 20 can be a miniaturized strain gauge, a MEMS (micro electrical mechanical system) sensor, a surface acoustic wave (SAW) sensor, or a capacitance-type sensor adapted to measure strain in an element, or any other strain sensor capable of measuring both static and dynamic strain in a loaded element 1. Each of the aforementioned sensors 20 consume relatively little electrical power and thus are advantageous for use in the instant system 20 when an in vivo application is necessary.

Referring to FIG. 2, a capacitance-type cantilevered beam sensor 20 may be employed with the present invention, wherein a capacitance beam 22 acting as a first parallel plat depends from a pivot 24 secured to a slipcover 26 that permits the sensor to be mounted on the strained element 1, or alternatively on a housing encapsulating the sensor 20, in addition to acting as the second parallel plat of the sensor 20. As the element 1 flexes, the distance between the beam 22 and slipcover 26 varies, thereby varying the capacitance of the sensor.

The sensor 20 is thus capable of measuring the deformation or curvature of element 1 as it is subjected to varying loads. As element 1 is loaded its surface deforms, typically such deformation being in the nature of a convex or concave curvature, thereby changing the capacitance between beam 22 and element 1. Alternatively, a sensor 20 capable of measuring static and dynamic strain may be employed in place of a capacitive beam sensor, since the variable strain signal produced thereby is representative of surface deformation as element 1 flexes or curves.

Referring again to FIG. 1, a passive telemetry circuit 40 is provided (requiring no battery) that includes an inductor $L_R$ and capacitor $C_R$ forming a simple tank circuit. The reader module utilizes an antenna coil 62 that transmits at a predetermined frequency, for example 125 KHz, as is common in radio frequency identification device (RFID) circuitry. The power transmitted from the antenna 62 inductively couples the telemetry circuit 40, thereby causing it to resonate at a particular frequency depending upon the inductance and capacitance values.

As the capacitance of the strain sensor $C_L$ varies with the strain as measured in element 1, the resonant frequency of the telemetry circuit 40 changes responsive to the strain. The reader 60 then detects the corresponding resonant frequency signal produced by the telemetry circuit 40 that is indicative of strain in the element 1.

In one embodiment of the invention, a simple power circuit 44 is included to provide rectified dc power derived from the power transmitted from the reader antenna 62 to the telemetry circuit 40 to be utilized to power additional circuitry such as signal processing (not shown) for the sensor 20 signal.

Referring to FIG. 3, an alternative telemetry circuit 40 is shown, whereby a miniature power supply 46, for example a lithium battery, is used to actively power the telemetry circuit 40. A real time clock 48 is used as a switch to energize and de-energize the entire circuit 40 at predetermined intervals in order to preserve battery 46 power. In this embodiment of the invention a transceiver integrated circuit (IC) 50 is used to accept the sensor 20 input 22 and transmit the input to the remote reader 60. This embodiment of the present invention permits the use of a conventional strain gauge as a sensor 20, since sufficient dc power is readily available from the battery 46, as well as on-board microcontroller for processing and storing the data from the sensor 20. The sensor 20 data is then transmitted via radio frequency communication through an antenna 52. This embodiment of the present invention also permits the use of a variety of commercially available IC packages as a transceiver 50 for use in storing and transmitting the sensor 20 data.

Figure 4:
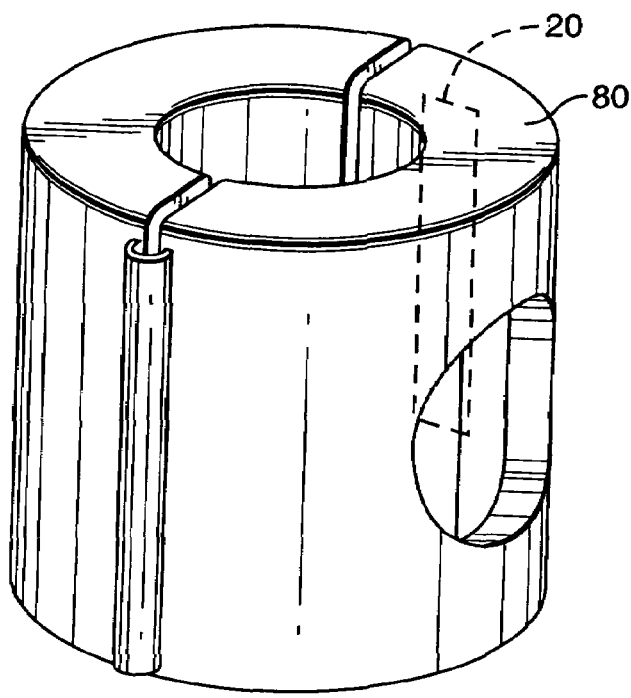
FIG. 4 is an isometric view of a sensor housing in accordance with the present invention.
Figure 5:
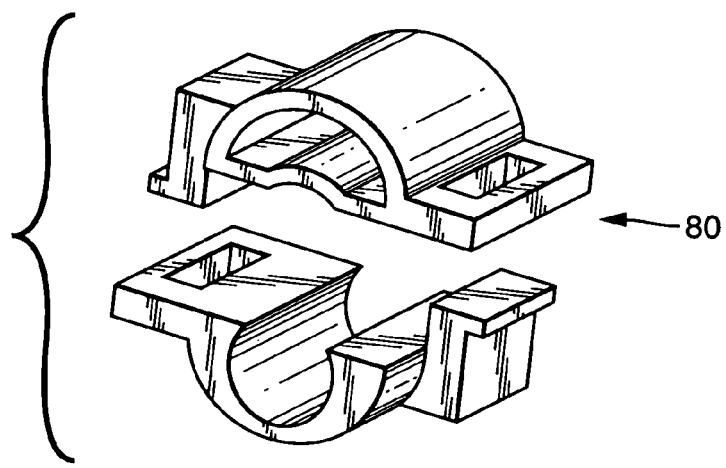
FIG. 5 is an isometric view of a sensor housing in accordance with the present invention.
Figure 6:
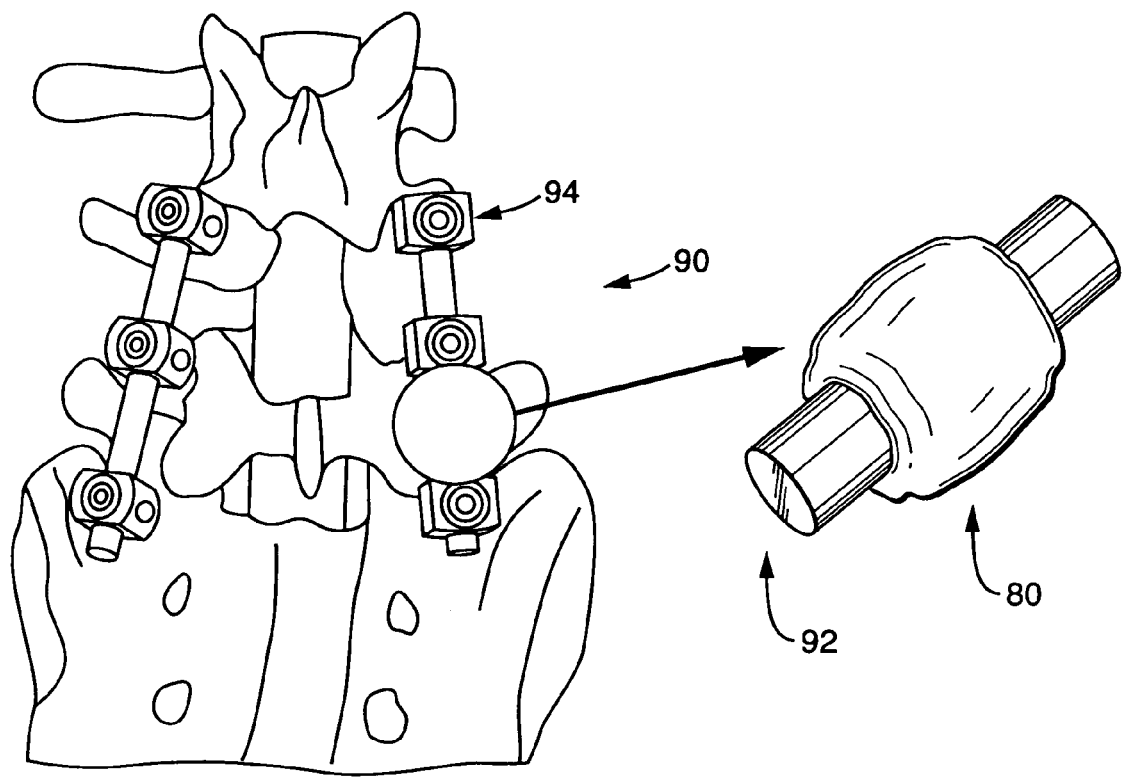
FIG. 6 is a diagram of a spinal fusion orthopedic implant equipped with the present invention.

FIGS. 4 and 5 depict two housings 80 that may be used to encapsulate the sensor 20 and telemetry circuit, and are advantageous for use in inter-vivo applications. These housings 80 are suitable for use where the sensor 20 is sued to measure strain in a rod or similar device, for example as a component of an orthopedic implant. As one example of orthopedic use, FIG. 6 shows a spinal fusion implant 90 comprising a plurality of rods 92 affixed by a plurality of pedicle screws 94 both above and below a pair of vertebrae being fused. This orthopedic implant 90 is used to stabilize and support the surgically fused vertebrae until the healing process fuses the vertebrae sufficiently to bear the load required of the spine. Over time as the fused vertebrae heal, there is an in vivo load transfer from the implant 90 to the spine. Thus by monitoring the strain in the implant rods 92 over time, a physician can determine the progression of the spinal fusion.

Figure 7:
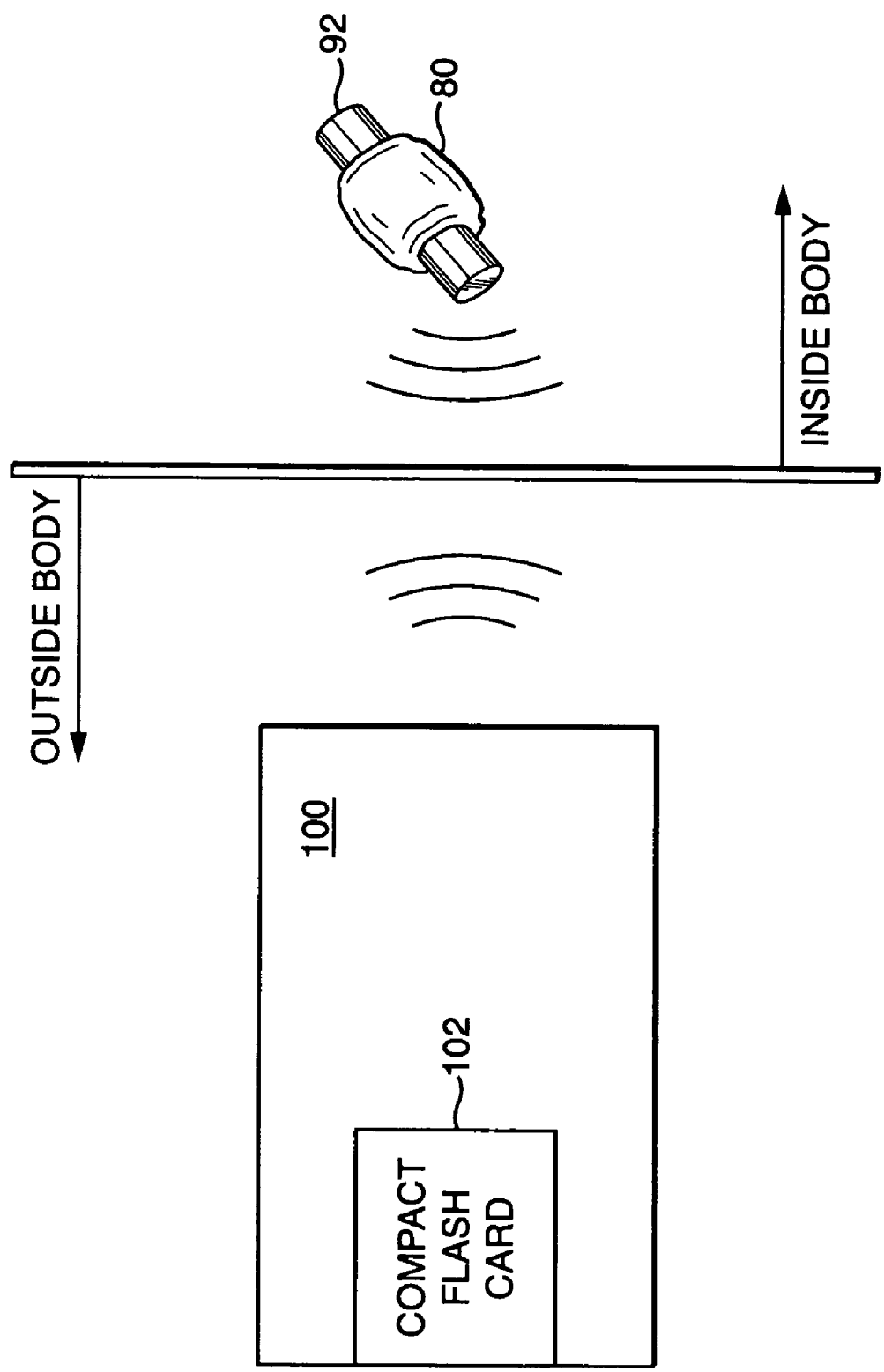
FIG. 7 is a block diagram of the system of the present invention.
Figure 8:
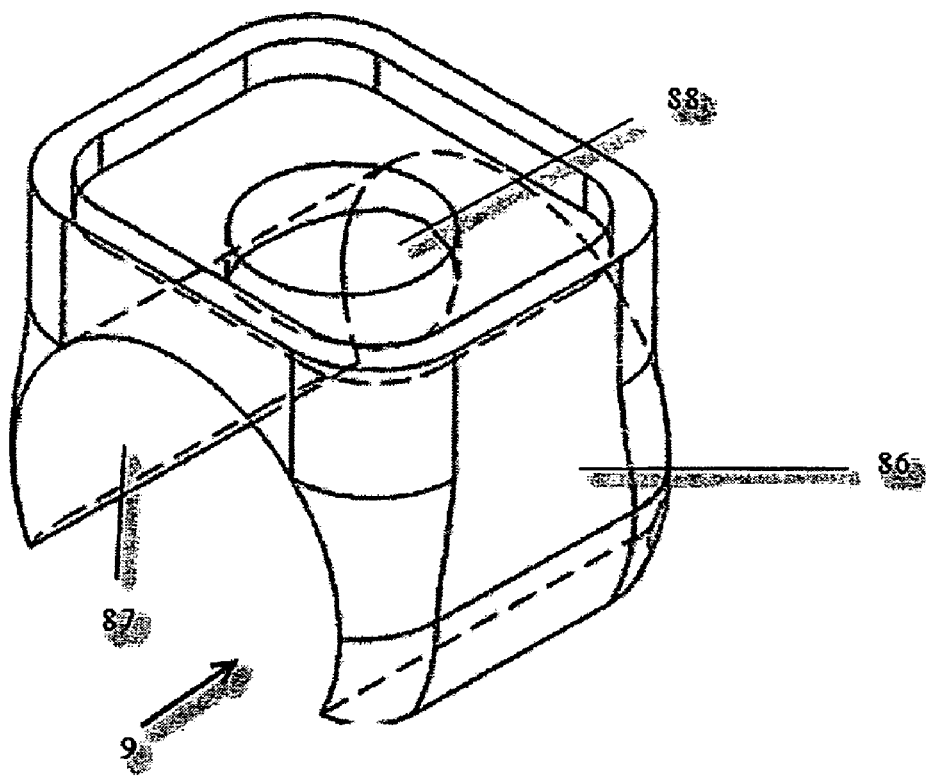
FIG. 8 is an isometric view of a sensor housing in accordance with one embodiment of the present invention.

The housings 80 may be made of any bio-compatible material such as polyethylene or a similar non-reactive polymer to permit the sensor 20 and telemetry circuit 40 encapsulated therein to be implanted in a living organism. As best seen in FIGS. 6 and 7 the substantially annular housings 80 can be placed around the circumference of an implant rod 92 such that the sensor 20 is disposed on the rod 92 surface. Furthermore, the housings 80 may comprise two interlocking halves to facilitate the placement of the telemetry circuit 40 and sensor 20 within the housing, and permit ease of installation of the entire assembly onto an implant rod. This feature of the invention permits a sensor 20 and concomitant telemetry circuit 40 to be affixed to the implant rod or rods 92 in advance of the surgery, thereby reducing operating time. While the specific housing embodiments shown in FIGS. 4 and 5 are adapted to be used with cylindrical rods, it will be appreciated by one or ordinary skill that a variety of implant shapes can be accommodated by modification of the interior surface of the housing 80.

Figure 9:
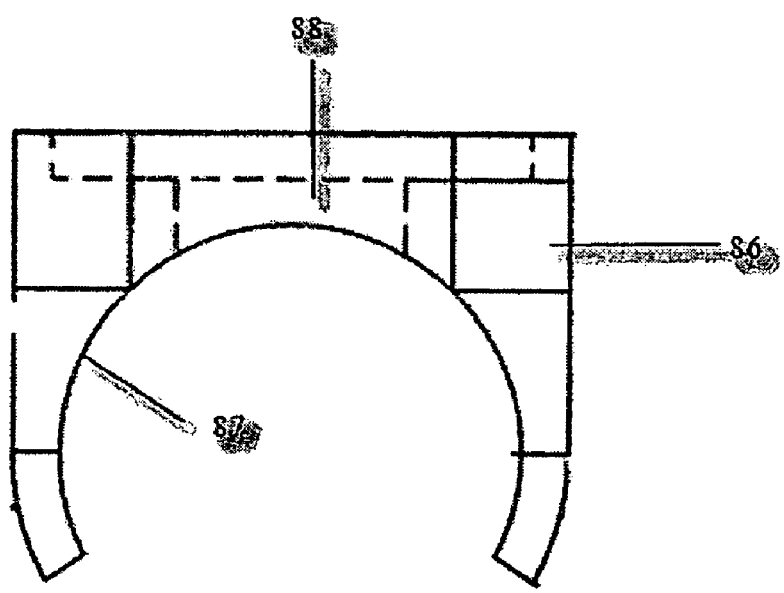
FIG. 9 is a view of a sensor housing taken in the direction of arrow 9 of FIG. 8.
Figure 10:
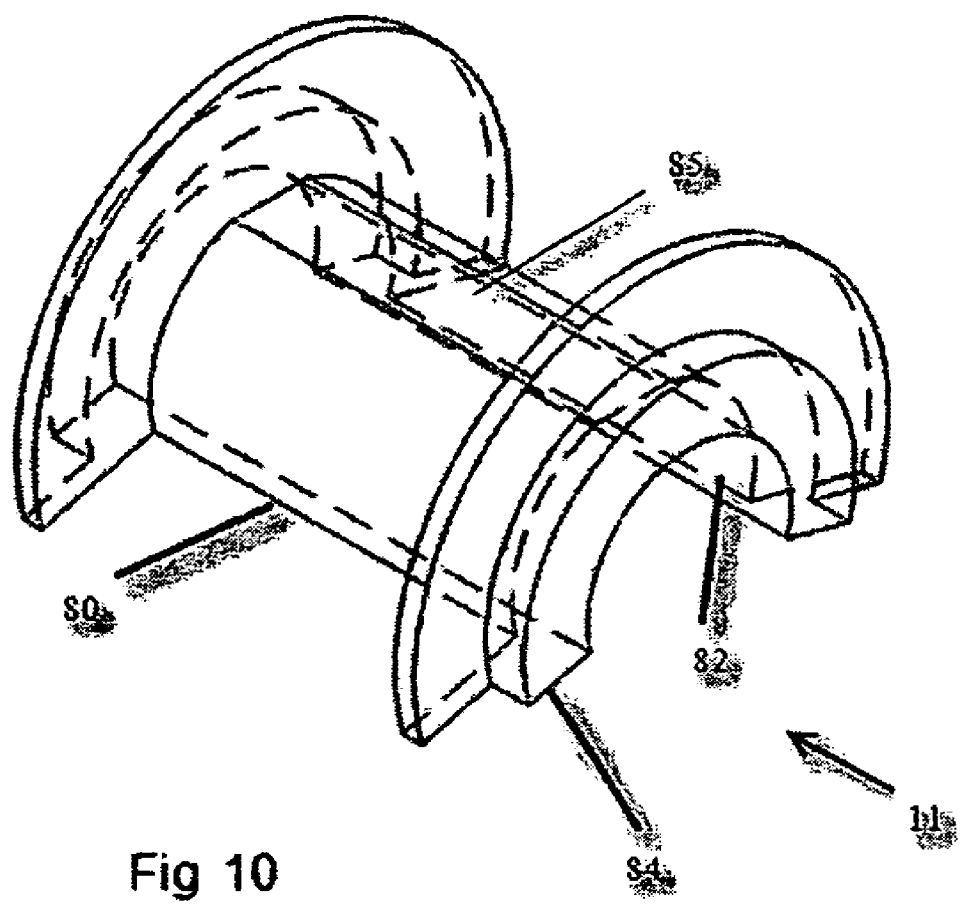
FIG. 10 is an isometric view of a sensor housing in accordance with one embodiment of the present invention.
Figure 11:
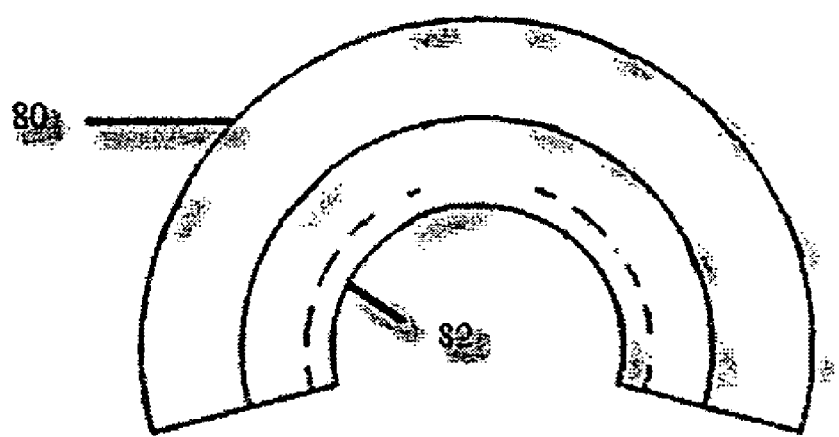
FIG. 11 is a view of a sensor housing taken in the direction of arrow 11 of FIG. 10.

Drawing FIGS. 8-11 depict an alternative housing 80 which is shaped as a truncated annulus having an interior surface 82 that conforms closely to the exterior shape of element 1 or rods 92, thereby facilitating placement around a portion of cylindrical rods 92. As best seen in FIGS. 9 and 11, the housing 80 further comprises annular side portions 84 that extend more than half way around the circumference of rod 92. This feature of the invention permits the housing 80 and concomitant sensor 20 to be snapped into place over rod 92, thereby facilitating installation. While interior surfaces 82 are shown as generally annular in shape, any shape required to mate with rod 92 or element 1 may be employed as an interior surface shape. Housing 80 may also include a flat portion 85 on an exterior surface thereof, to permit positive placement of sensor 20 thereon.

As best seen in FIGS. 9 and 10 a housing cover 86 may comprise a mating surface 87 that permits housing cover 86 to closely mate with the exterior surface of housing 80. Housing cover 86 also includes an aperture 88 in an interior portion thereof that provides room for antenna 62 and sensor 20 that is disposed on flat portion 85 of housing 80. This feature of the invention permits sensor 20 and concomitant electronic components to be situated on housing 20 flat portion, thence covered and sealed from damage by housing cover 86. While mating surface 87 of cover 86 and interior surface 82 of housing 80 are shown as generally annular in shape, a wide variety of complementary surface shapes may be employed without departing from the scope of the present invention.

Additionally, the sensor 20 may be placed so that it does not directly contact the surface of the implant rod 90, but instead is in contact with the interior surface of the housing 80. As the rod 90 is strained, the housing 80 is also strained, thereby imparting strain to the sensor 20, and even amplifying the strain in the rod 90 to some extent.

In a further embodiment of the invention a compact battery-powered reader 100 and an associated flash card memory 102 may be employed as a belt or pocket unit, similar to a conventional pager, that may be located on a belt or other location proximate to an implanted orthopedic device instrumented with the invention. The compact reader 100 provides sufficient power to the sensor 20 and telemetry circuit 40 to receive sensor 20 data at pre-determined intervals throughout the day whereupon it is stored in the memory 102. The flash memory card 102 may be removed from the reader 100 periodically, and the data stored thereon may be downloaded to a conventional computer (not shown) for use by a physician. This feature of the invention permits the physician to monitor in near real-time the progress of the fusion process, or other strain data indicative of the progress of orthopedic implant surgery. Furthermore, since the flash memory card 102 can be readily used to transmit the stored strain data to a conventional personal computer, the physician can have near real-time access to the data in event of an emergency or related concern from a recovering patient.

Additionally, a conventional microcomputer control module 110 may be employed in a communication with the reader 60 to store and process the sensor 20 data and may be used to construct graphical representations of the strain data, or transmit the data to others.

We claim:
1. A system for measuring and remotely monitoring the change in curvature in an element comprising:
   a sensor for measuring the change in curvature in said element producing an electrical signal representative thereof;
   a bio-compatible housing for encapsulating said sensor and contacting said element, whereby said housing transmits said change in curvature of said element to said sensor; and
   a telemetry circuit electrically coupled to said sensor for encoding and transmitting the signal representative of said change in curvature.
2. A system for measuring and remotely monitoring the change in curvature in an element as claimed in claim 1 further comprising:
   a housing for encapsulating said sensor and said telemetry circuit having an interior surface for contacting said element whereby said housing transmits said change in curvature of said element to said sensor.
3. The system for measuring and remotely monitoring the change in curvature in an element as claimed in claim 1 wherein said sensor for measuring change in curvature is a cantilever beam type capacitive sensor.
4. The system for measuring and remotely monitoring the change in curvature in an element as claimed in claim 2 wherein said housing is substantially annular for placement around an orthopedic implant rod.
5. The system for measuring and remotely monitoring the change in curvature in an element as claimed in claim 2 comprising:
   a truncated annular housing having an interior surface that conforms closely to an exterior surface of said element whereby said change in curvature thereof is transmitted through said annular housing to said sensor.
6. The system for measuring and remotely monitoring the change in curvature in an element as claimed in claim 5 comprising:
   a truncated annular housing having side portions shaped to conform to an orthopedic implant exterior surface whereby said annular housing is pressure-fitted onto said implant.
7. The system for measuring and remotely monitoring the change in curvature in an element as claimed in claim 6 wherein said orthopedic implant comprises a rod.
8. The system for measuring and remotely monitoring the change in curvature in an element as claimed in claim 6 wherein said orthopedic implant comprises a plate.
9. The system for measuring and remotely monitoring the change in curvature in an element as claimed in claim 6 wherein said orthopedic implant comprises a pedicle screw.
10. The system for measuring and remotely monitoring the change in curvature in an element as claimed in claim 6 wherein said orthopedic implant comprises a joint implant.
11. The system for measuring and remotely monitoring the change in curvature in an element as claimed in claim 2 comprising:
    a housing having a flat portion on an exterior surface thereof for mounting said sensor thereto.

* * * * *

UNITED STATES PATENT AND TRADEMARK OFFICE
CERTIFICATE OF CORRECTION

| | | |
|---|---|---|
| PATENT NO. | : 7,357,037 B2 | Page 1 of 1 |
| APPLICATION NO. | : 11/226023 | |
| DATED | : April 15, 2008 | |
| INVENTOR(S) | : William P. Hnat, John E. Naber and Kevin M. Walsh | |

It is certified that error appears in the above-identified patent and that said Letters Patent is hereby corrected as shown below:

Please insert the following after column 1, line 10 and before "FIELD OF THE INVENTION":

--STATEMENT REGARDING FEDERALLY SPONSORED RESEARCH OR DEVELOPMENT

This invention was made with government support under Contract No. BES-0097521 awarded by the National Science Foundation. The government has certain rights in this invention.--

Signed and Sealed this
Twelfth Day of March, 2013

Teresa Stanek Rea
*Acting Director of the United States Patent and Trademark Office*